United States Patent
O'Connell (12) 
(10) Patent No.: US 6,267,776 B1
(45) Date of Patent: Jul. 31, 2001

(54) VENA CAVA FILTER AND METHOD FOR TREATING PULMONARY EMBOLISM

(76) Inventor: Paul T. O'Connell, 2414 Harrison St., Evanston, IL (US) 60201

(*) Notice: Subject to any disclaimer, the term of this patent is extended or adjusted under 35 U.S.C. 154(b) by 0 days.

(21) Appl. No.: 09/304,311

(22) Filed: May 3, 1999

(51) Int. Cl.$^7$ .......................... A61M 29/00; A61B 17/08
(52) U.S. Cl. .......................................... 606/200; 606/158
(58) Field of Search .................................. 606/200, 198, 606/194, 1, 108, 195, 191, 152–155, 158; 623/1.1–1.22; 604/104, 106

(56) References Cited

U.S. PATENT DOCUMENTS

| 2,281,448 | 4/1942 | Mathey | 220/86 |
| 3,334,629 | 8/1967 | Cohn | 128/325 |

(List continued on next page.)

FOREIGN PATENT DOCUMENTS

| 0 565 395 A1 | 10/1993 | (EP) | A61F/2/02 |
| 0 809 981 A1 | 3/1997 | (EP) . | |
| 2 718 950 | 10/1995 | (FR) | A61F/2/01 |
| 2 768 326 | 3/1999 | (FR) | A61F/2/01 |

OTHER PUBLICATIONS

PCT Search Report for Application No. PCT/US00/12004 transmitted Sep. 13, 2000.
Crochet et al., Vena Tech–LGM filter: Long Term Results of a Prospective Study, Radiology, 1993, vol. 188, pp. 857–860.
Murphy et al., LGM Vena Cava Filter: Objective Evaluation of Early Results, Journal of Vascular and Interventional Radiology, 1991, vol. 2, pp. 107–115.
Taylor et al., Vena Tech Vena Cava Filter: Experience and Early Follow–Up, Journal of Vascular and Interventional Radiology, 1991, vol. 2, pp. 435–440.
Cull et al., The Vena Tech Filter: Evaluation of a New Inferior Vena Cava Interruption Device, The Journal of Cardiovascular Surgery, 1991, vols. 32–50, pp. 691–696.
Ricco et al., Percutaneous Transvenous Caval Interruption with the "LGM" Filter: Early Results of a Multicenter Trial, Annals of Vascular Surgery, 1988, vol. 3, 242–247.
Mohan et al., Comparative Efficacy and Complications of Vena Caval Filters, Journal of Vascular Surgery, 1995, vol. 21–20, pp. 235–246.
Ricco et al., The LGM Vena Tech Caval Filter: Results of a Multicenter Study, Annals of Vascular Surgery, 1995, vol. 59, pp. 89–100.
Grassi et al., Vena Caval Occulusion After Simon Nitonal Filter Placement: Identification with MR Imaging in Patients with Malignancy, JVIR, 1992, vol. 3, pp. 535–539.
Johnson et al., CT of Greenfield Filters, 16th Annual Meeting SCVIR, 1991, pp. 167.
Sweeny et al., Deployment Problems with the Titanium Greenfield Filter, JVIR, 1993, vol. 4, pp. 691–694.

(List continued on next page.)

*Primary Examiner*—Gary Jackson
*Assistant Examiner*—(Vikki) Hoa B. Trinh
(74) *Attorney, Agent, or Firm*—Marshall, O'Toole, Gerstein, Murray & Borun (57) ABSTRACT

A filter is provided that is convertible from a filter configuration to an open, stent-like configuration. The filter includes a plurality of intraluminal filter elements (filter legs) that may be formed into a single cone or dual cone filter structure. A retainer secures the filter legs in the filter configuration upon initial deployment within a vessel. The retainer is then either self-releasing or removable to permit the filter legs to expand from the filter configuration into what may generally be described as an open or stent-like configuration.

62 Claims, 5 Drawing Sheets

U.S. PATENT DOCUMENTS

| | | | |
|---|---|---|---|
| 3,540,431 | 11/1970 | Mobin-Uddin | 128/1 |
| 3,868,956 | 3/1975 | Alfidi et al. | 128/345 |
| 3,952,747 | 4/1976 | Kimmell, Jr. | 128/303 |
| 4,425,908 | 1/1984 | Simon | 128/1 |
| 4,494,531 | 1/1985 | Gianturco | 128/1 |
| 4,643,184 | 2/1987 | Mobin-Uddin | 128/303 |
| 4,657,543 | 4/1987 | Langer et al. | 604/891 |
| 4,688,553 | 8/1987 | Metals | 128/1 |
| 4,727,873 | 3/1988 | Mobin-Uddin | 128/303 |
| 4,781,177 | 11/1988 | Lebigot | 128/897 |
| 4,817,600 | 4/1989 | Herms et al. | 128/303 |
| 4,873,978 | 10/1989 | Ginsburg | 128/345 |
| 4,990,156 | 2/1991 | Lefebvre | 606/200 |
| 5,059,205 | 10/1991 | El-Nounou et al. | 606/200 |
| 5,108,418 | 4/1992 | Lefebvre | 606/200 |
| 5,133,733 | 7/1992 | Rasmussen et al. | 606/200 |
| 5,152,777 | 10/1992 | Goldberg et al. | 606/200 |
| 5,242,462 | 9/1993 | El-Nounou et al. | 606/200 |
| 5,324,304 | 6/1994 | Rasmussen | 606/200 |
| 5,344,427 | 9/1994 | Cottenceau et al. | 606/200 |
| 5,370,657 | 12/1994 | Irie | 606/200 |
| 5,375,612 | 12/1994 | Cottenceau et al. | 128/899 |
| 5,383,887 | 1/1995 | Nadal | 606/200 |
| 5,415,630 | 5/1995 | Gory et al. | 604/53 |
| 5,443,478 | 8/1995 | Purdy | 606/200 |
| 5,484,424 | 1/1996 | Cottenceau et al. | 604/282 |
| 5,514,154 | 5/1996 | Lau et al. | 606/195 |
| 5,527,338 | 6/1996 | Purdy | 606/200 |
| 5,540,680 | 7/1996 | Guglielmi et al. | 606/32 |
| 5,601,595 | 2/1997 | Smith | 606/200 |
| 5,618,563 | 4/1997 | Berde et al. | 424/501 |
| 5,624,449 | 4/1997 | Pham et al. | 606/108 |
| 5,626,605 | 5/1997 | Irie et al. | 606/200 |
| 5,630,801 | 5/1997 | Roussigne et al. | 604/95 |
| 5,634,942 | 6/1997 | Chevillon et al. | 623/1 |
| 5,669,905 | 9/1997 | Scheldrup et al. | 606/32 |
| 5,670,161 | 9/1997 | Healy et al. | 424/426 |
| 5,693,067 | 12/1997 | Purdy | 606/200 |
| 5,713,853 | 2/1998 | Clark et al. | 604/53 |
| 5,725,550 | 3/1998 | Nadal | 606/200 |
| 5,743,905 | 4/1998 | Eder et al. | 606/32 |
| 5,746,767 | 5/1998 | Smith | 606/200 |
| 5,755,790 | 5/1998 | Chevillon et al. | 623/12 |
| 5,792,400 | 8/1998 | Talja et al. | |
| 5,800,457 | 9/1998 | Gelbish | 606/200 |
| 5,810,874 | 9/1998 | Lefebvre | 606/200 |
| 5,836,968 | 11/1998 | Simon et al. | 606/200 |
| 5,836,969 | 11/1998 | Kim et al. | 606/200 |
| 5,843,118 | 12/1998 | Sepetka et al. | 606/194 |
| 5,853,420 | 12/1998 | Chevillon et al. | 606/200 |
| 5,893,869 | 4/1999 | Barnhart et al. | 606/200 |
| 6,080,178 * | 6/2000 | Meglin | 606/200 |

OTHER PUBLICATIONS

Milward et al., LGM (Vena Tech) Vena Caval Filter: Experience at a Single Institution, JVIR, 1994, vol. 5, pp. 351–356.

Roehm et al., The Bird's Nest Inferior Vena Cava Filter: Progress Report, Radiology, 1988, vol. 168, pp. 745–749.

B. Braun Medical, Vena Tech Division, A Patient's Guide to the Vena Tech LGM Vena Cava Filter.

Coleman, Overview of Interruption of the Inferior Vena Cava, Seminars in Interventional Radiology, Sep. 1996, vol. 3, pp. 175–187.

Kraimps et al., Optimal Central Trapping (OPCETRA) Vena Caval Filter: Results of Experimental Studies, JVIR, Nov. 1992, pp. 697–701.

Kraimps et al., Conical Endocaval Filters with Metallic Struts: Search for a New Model, Annals of Vascular Surgery, 1992, vol. 6, pp. 99–110.

Crochet et al., Caval Incorporation of the LGM Vena Tech Filter: An Experimental Study, JVIR, May–Jun. 1997, pp. 419, 425.

Simon et al., Simon Nitonol Inferior Vena Cava Filter: Initial Clinical Experience, Radiology, vol. 172, pp. 99–103.

Grassi, Inferior Vena Caval Filters: Analysis of Five Currently Available Devices, AJR, Apr. 1991, vol. 156, pp. 813–821.

Dorfman, Percutaneous Inferior Vena Caval Filters, Radiology, 1990, vol. 174, pp. 987–992.

Greenfield et al., Results of a Multicenter Study of the Modified Hook–Titanium Greenfield Filter, Journal of Vascular Surgery, 1991, vol. 14, pp. 253–257.

Greenfield et al., Twelve–Year Clinical Experience with the Greenfield Vena Caval Filter, Surgery, Oct. 1988, pp. 706–712.

Wang et al., Use of a Nitinol Gooseneck Snare to Open an Incompletely Expanded Over–the Wire Stainless Steel Greenfield Filter, AJR, Feb. 1999, vol. 172, pp. 499–500.

* cited by examiner

VENA CAVA FILTER AND METHOD FOR TREATING PULMONARY EMBOLISM

BACKGROUND OF THE INVENTION

1. Field of the Invention

The invention relates generally to devices for the prevention of pulmonary embolism and, more particularly, the invention relates to a filter device for placement within the inferior vena cava that is operable to prevent embolus migration.

2. Description of the Related Technology

Blood coagulation, or clotting, is the transformation of blood from a fluid initially into a semi-solid gel and ultimately into an organized, fibrinous solid. Coagulation is the body's mechanism to control and stop unwanted bleeding. Despite the desirable and necessary effects of blood clotting, several undesirable effects may result from clotting which can lead to serious medical disorders and, in some instances, death. One example of such an undesirable effect of clotting is deep vein thrombosis (DVT), the formation of blood clots within the veins of the legs. DVT which is not diagnosed and successfully treated can result in the migration of blood clots to the pulmonary arteries in the lungs, arresting blood flow through the lungs (pulmonary embolism). Pulmonary embolism is one of the most common causes of death for hospitalized patients, and results in more than 200,000 deaths annually in the United States.

The disease process in which blood clots form within a vein and subsequently migrate through the venous system to the pulmonary circulation is called venous thromboembolic disease. Numerous factors, acting independently or simultaneously, can cause clot formation within a vein and, potentially, thromboembolism: (1) damaged or irregular surfaces on the inside of the vein can lead to thrombus formation, (2) imbalances in the body's natural clotting-lytic (clot-dissolving) systems can trigger clot formation, (3) slowly-moving blood or blood passing through an area of turbulence within the vein, such as that in blood pooled in damaged leg veins, is likely to clot, and (4) the release of clotting factors into the blood from traumatized tissue is likely to trigger widespread clotting.

Various methods have been developed to treat venous thromboembolic disease. Anticoagulant drugs ("blood thinners") slow the process of blood coagulation. Anticoagulants such as heparin and its low-molecular weight variants as well as warfarin, are the front-line treatment for deep vein thrombosis and pulmonary embolism, and are largely successful. Some patients, in particular those with extensive clotting which threatens to damage the deep veins, are treated with enzymes known collectively as thrombolytics which actively break down existing clots. However, some patients cannot be successfully treated with anticoagulants or thrombolytics because clots continue to form in spite of adequate dose levels of these drugs. Other patients cannot be given anticoagulants or thrombolytics due to other medical conditions.

For patients in whom anticoagulation has failed or to whom it cannot be administered, it was necessary to develop alternative treatments to prevent pulmonary embolism. One of the earliest surgical solutions was ligation of the common femoral vein to prevent the migration of clots from the large veins in the upper leg to the lungs. Then, in the mid 1940s, Oschner and DeBakey and O'Neil proposed ligating the inferior vena cava (the large central vein in the abdomen) in order to prevent emboli from migrating from the legs or pelvic area to the pulmonary circulation. While effective in preventing pulmonary embolism, this technique resulted in complications due to diminished blood return to the right heart.

To avoid employing ligation techniques, vein clips and, subsequently, blood filters were developed to prevent pulmonary embolism. Vein clips are intended to be placed around the vein during an open surgical procedure, and such clips reduce the area within the vein available for blood flow to one or several small channels to prevent clots from passing through to the pulmonary circulation. Blood filters are implanted within the vein, typically the inferior vena cava, and are intended to trap large blood clots while allowing blood to pass freely through the filter around the clot. In most cases trapped blood clots will normally dissolve over time.

Blood filters (vena cava filters) are placed within the inferior vena cava lumen from a variety of peripheral vein access sites, for example, the jugular or femoral veins. An early example of such a filter was the Mobin-Uddin (MU) umbrella filter, which was developed and made available by American Edwards Laboratories in Santa Monica, Calif. in the 1970s. The Mobin-Uddin umbrella was composed of six flat ELGILOY spokes radiating from a hub and partially covered by a web designed to capture blood clots. MU filters were introduced into the body via a cutdown of the jugular or femoral vein and subsequent passing of a catheter through the access site to the filter implant site in the infrarenal inferior vena cava. While this method was an improvement over previous methods, the MU filter was associated with a high incidence of occlusion of the inferior vena cava, in which blood flow through the vena cava was completely obstructed.

In the mid 1970's, the Kimray-Greenfield (KG) vena cava filter was introduced. The original KG filter is conical in shape and is composed of six stainless steel wires equally spaced with its apex cephalad. Although the filter was originally placed using a local cutdown of the jugular or femoral vein, it was later adapted to be inserted percutaneously. The KG filter is designed to capture clots 7 mm or greater in diameter, holding the clots in the infrarenal vena cava until the body's own lytic system dissolves the clot. The principal drawbacks of the KG filter are the possibility of tilting and filter migration, often related to a failure to open, or untimely ejection of the filter from the introducer.

Subsequent versions of the so-called Greenfield filter were developed to reduce the size of the introducer catheter to facilitate percutaneous introduction. Other vena cava filters were introduced in the United States in the late 1980s, including the Vena Tech—LGM vena cava filter, the Bird's Nest vena cava filter, and the Simon-Nitinol vena cava filter. The Vena Tech—LGM filter is a conical filter made from the PHYNOX alloy, with longitudinal stabilizing legs in addition to the intraluminal cone. The Bird's Nest filter is a "nest" of stainless steel wire which is wound into the vena cava, while the Simon Nitinol filter is a two-stage filter made from nickel-titanium alloy with a conical lower section and a petal-shaped upper section. All of these devices are permanent implants which cannot be removed from the body without a major surgical intervention.

Among numerous vena cava filters introduced in Europe but never brought to the United States was the optimal central trapping (OPCETRA) filter. The OPCETRA filter has two main parts: a main basket with ten, long stainless steel wire arms and a distal basket with five, short stainless steel wire arms. This design gives the filter an hourglass shape which provides a self-orienting structure for the filter within the lumen of a blood vessel. The OPCETRA filter was also a permanently implanted vena cava filter.

All of the above-identified vena cava filters are inserted into the body by passing the filter through a catheter to the site of deployment in the infrarenal inferior vena cava. After ejection from the catheter, these filters open or are manually deployed until the filter anchoring elements engage the vessel wall. These filters often have hooks or some other means by which the filter becomes fixed permanently to the vessel wall.

For an important subset of patients, in particular young trauma patients and patients undergoing total hip or knee replacement surgery, the risk of pulmonary embolism is short-term and limited to a definable period of time. Because of the long-term risks associated with implantation of a permanent vena cava filter, including venous stasis due to caval occlusion and its related complications, patients whose risk period is limited are not considered good candidates for permanent vena cava filters. The search for an appropriate temporary therapy for such patients lead to the development of temporary, tethered removable vena cava filters.

Tethered temporary vena cava filters are attached to a catheter and are implanted in the infrarenal vena cava with the tethering catheter extending out of the puncture site in the neck or groin, or buried subcutaneously within the soft tissues in the patient's neck. The tether remains coupled to the filter after deployment. The tether is then used to retrieve the filter. The potential for septic complications associated with the tethering catheter exiting the neck or groin require removal of such devices within fourteen days of placement. Risk periods for pulmonary embolism in such patients, however, can extend up to twenty-one weeks.

Temporary retrievable filters which are not attached to a tethering catheter have a construction similar to some versions of permanent filters. A hook or similar grasping structure is provided to allow a snare to engage the filter during the retrieval procedure. The filter in its entirety is then retrieved using a snare by drawing it into a catheter. However, to ensure the filter does not migrate within the vessel, barbs, anchors or similar structures must be used to engage the filter with the interior wall of the vessel for retaining it in place. These anchors make removal without injuring the vessel difficult. Moreover, after a relatively short period of time the portion of the filter legs in contact with the vessel wall are incorporated by endothelial tissue making retrieval difficult or impossible.

More recently, it has been proposed to provide a removable filter in two parts. An anchoring part of the filter engages the vessel walls, and become incorporated by endothelial tissue. A filter part is releasably coupled to the anchoring part. After the risk of embolism has passed, the filter part may be retrieved using a snare and catheter.

As of the time of the invention, there are no temporary or retrievable vena cava filters approved for use in the United States. The complications associated with permanent vena cava filters, tethered temporary filters and retrievable filters demonstrate that there remains a need for a filter device for use in treating the risk of embolism from the inferior venous system that overcomes the limitations of the present designs of permanent and temporary filter devices.

SUMMARY OF THE INVENTION

The invention provides a filter arranged to be disposed within a blood vessel. The filter includes intraluminal filter elements and is convertible from a filter configuration to an open, stent-like configuration.

The invention also provides a method of treating pulmonary embolism using a filter constructed in accordance with the invention.

In a preferred embodiment, the filter device includes a plurality of elements that are formed into a single cone or dual cone filter structure. A retainer secures the elements in an intraluminal filter configuration upon initial deployment within a vessel. The retainer is then either self-releasing or removable to permit the legs to expand from the filter configuration into what may generally be described as an open or stent-like configuration substantially, totally reopening the lumen.

To maintain stability within the lumen, superior and/or inferior ends of the filter can be formed with a small barb or hook that engages the interior wall of the vessel.

A single cone filter in accordance with the invention includes a plurality of intraluminal filter elements, the superior ends of which are joined by a releasable retainer. In one preferred embodiment, the single cone filter has filter legs which are constrained in the filter configuration. In another preferred embodiment, a spring member couples to the legs of the single cone filter to urge them radially outward and revert the filter to an open or stent-like configuration. When in the open configuration, the lumen is substantially unobstructed by the filter.

A dual cone filter in accordance with a preferred embodiment of the invention has intraluminal filter elements joined by a releasable retainer at a location between their superior and inferior ends. This dual cone shape advantageously improves the self-orienting mechanism of the filter. A spring may join the legs to urge them from the dual cone or hourglass shape into a stent-like configuration upon release of the retainer. Alternatively, the legs may be formed to provide the restoring force.

In various aspects of the invention, the retainer can be either passively or actively releasable. The retainer can be made from a metal or a biodegradable material. With either embodiment, once the retainer is removed, either actively by retrieving the retainer using a snare or passively after sufficient biodegradation of the retainer, the legs revert into the stent-like configuration.

In still another embodiment, the filter device has intraluminal elements made of a first biodegradable material and the releasable retainer made of a second biodegradable material. In this embodiment, the releasable retainer is composed of a material that degrades before the intraluminal elements which degrade at some later time. All the filter materials degrade, usually by hydrolysis, and are passed out of the body through the body's excretory system. Thus, all filter materials are removed from the body.

BRIEF DESCRIPTION OF THE DRAWINGS

The invention will be described with reference to the following detailed description of several preferred embodiments with reference to the drawings wherein like reference numerals are used to represent like elements, and in which.

DESCRIPTION OF THE PREFERRED EMBODIMENTS

Figure 1:
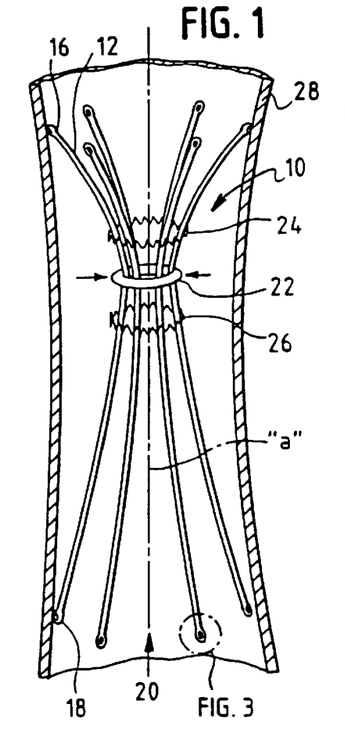
FIG. 1 is a side view of a filter in a filter configuration within a blood vessel and having a dual cone structure in accordance with a preferred embodiment of the invention.

Referring generally to FIGS. 1–11, and particularly to FIG. 1, a dual cone blood clot filtration device (filter) 10 in a filter configuration includes a plurality of intraluminal filter elements (filter legs) 12, which may be formed using a suitable wire. As used herein, the term "filter configuration" is used to refer to a filter according to the invention where the intraluminal filter elements are joined by a releasable retainer so as to form a filter structure within the lumen. The term "open configuration" or "stent-like configuration" is used to refer to a filter according to the invention where the releasable retainer has been removed, and the intraluminal filter elements are disposed substantially adjacent an interior wall of the lumen.

With continued reference then to FIG. 1, the filter legs 12 each have a blunted superior end 16 and inferior end 18. Superior and inferior are used in their ordinary sense to refer to the filter's position within the body. The superior ends 16 are positioned upstream relative to blood flow and the inferior ends 18 are positioned downstream relative to blood flow. The direction of blood flow is indicated in FIG. 1 by the arrow 20. The filter legs 12 are joined by a releasable retainer 22 at some location between the superior ends 16 and the inferior ends 18. In FIG. 1, the releasable retainer 22 secures the filter legs 12 in a dual cone filter configuration. The filter 10 may have a first spring 24 adjacent the superior ends 16 to urge them radially outwardly and a second spring 26 adjacent the inferior ends 18 to likewise urge them radially outward. Alternatively, the filter 10 may have a plurality of annular, horizontal members joining the filter legs 12. The releasable retainer 22 retains the filter legs 12 in the intraluminal dual cone filter configuration, e.g., resists the force exerted on the filter legs 12 by the first spring 24 and the second spring 26. The first spring 24 and the second spring 26 are each shown as an expanding annular spring, however, alternative spring configurations may be used, and several are described in connection with alternate preferred embodiments of the invention described below.

The filter 10 in FIG. 1 is shown inserted into a blood vessel 28 by a physician using the commonly practiced Seldinger technique. For percutaneous insertion of the filter 10, a vein is punctured with a needle, and a guidewire is advanced into the blood vessel 28 through the needle beyond the desired implantation site. A catheter consisting of an inner, dilating cannula within an outer sheath, up to 14 French in diameter, is then advanced into the vein, over the guidewire. When the desired implantation site is reached, the inner dilating cannula and guidewire are removed, leaving the sheath behind. The sheath acts as a conduit to permit the insertion of the filter. The filter 10, in a collapsed configuration, is introduced into the sheath and advanced to the implantation site. Once the filter 10 is in an appropriate position, the filter 10 is pushed out of the sheath or uncovered using a pushing catheter. Upon discharge, the filter legs 12 open and engage the interior wall of the blood vessel 28.

The filter legs 12 may be a flexible wire and, in one preferred embodiment, the wires are metallic and round. In such an embodiment, the wires are preferably a radiopaque and non-ferromagnetic metal which has been certified for use in permanently implanted medical devices by the International Standards Organization (ISO). The wires may, in particular, be a high cobalt, low ferrous alloy, such as that known as and sold under the registered trademarks of "PHYNOX" or "ELGILOY" which may have the composition, by weight percent: cobalt 42%, chromium 21.5%, nickel 18%, iron 8.85%, molybdenum 7.5%, manganese 2% with the balance made up of carbon and beryllium having a maximum of 0.15% carbon and 0.001% beryllium. The wires may also be composed of 316L stainless steel or alloys of nickel and titanium known to be shape-memory metals which are sold and manufactured under the trademark "NITINOL" or an alloy of tantalum. Filter devices 10 constructed from metals will preferably withstand twelve million respiratory cycles without mechanical failure and will be non-thrombogenic.

Figure 2:
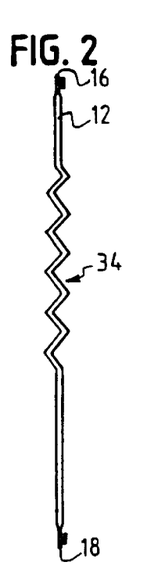
FIG. 2 is a view of an intraluminal filter element of the filter shown in FIG. 1 shown in an open configuration.

FIG. 2 shows a single filter leg 12 of the filter 10. The filter 10 and each filter leg 12 are constructed so as to eliminate the possibility of entrapping a guide wire during insertion of the filter 10 into the lumen of a blood vessel. When not being restrained by the releasable retainer 22, each filter leg 12 is relatively straight, running parallel to the axis of the vessel wall 28. Each blunted superior end 16 and interior end 18 end is flattened and has a small hook or barb 32, best seen in FIG. 3 and FIG. 4, that engages the interior wall of the blood vessel 28, which retain the filter 10 at a desired position within the blood vessel 28. Each filter leg 12 also includes a partially corrugated portion 34. Within a relatively short period of time after implantation, the small hooks or barbs 32 on the superior ends 16 and inferior ends 18 of the filter legs 12, which are in contact with the interior wall of the vessel 28, become permanently connected with the interior wall of the blood vessel 28. The corrugated portion 34 permits outward expansion of the filter leg 12 after release of the releasable retainer 22 without displacement of the superior end 16 or the inferior end 18 as the filter is converted to the stent-like configuration. This arrangement of the filter leg 12 prevents ripping or tearing of the interior wall of the blood vessel 28 upon opening of the filter 10 from the filter configuration shown in FIG. 1 to the open, stent-like configuration shown in FIG. 6. If the filter leg 12 did not include corrugated portion 34 upon release of the releasable retainer 22 and as the filter leg 12 tries to regain its original substantially straight shape, and with each superior end 16 and inferior end 18 engaging the blood vessel 28, this movement of the filter leg 12 may cause the superior end 16 and inferior end 18 to be pulled away from the interior wall of the vessel 28 resulting in injury to the vessel wall.

Figure 5:
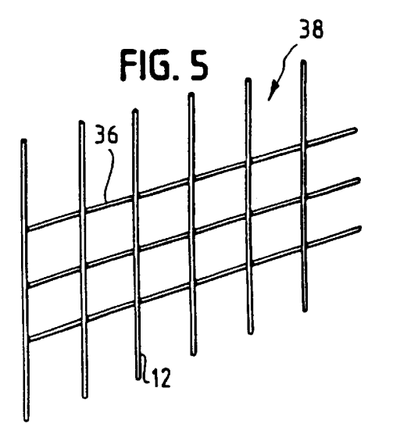
FIG. 5 is a view of the mesh of wires forming the filter illustrated in FIG. 1.
Figure 6:
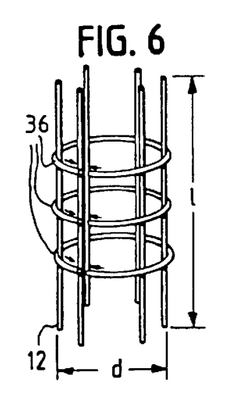
FIG. 6 is a side view of the filter illustrated in FIG. 1 and further shown in an open, stent-like configuration.
Figure 7:
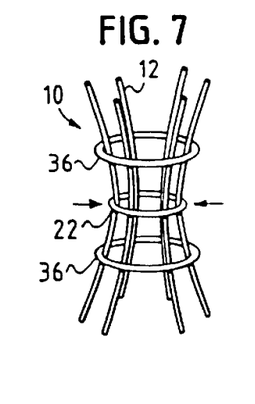
FIG. 7 is a side view of a filter similar to that shown in FIG. 1 and illustrating a releasable retainer restraining the plurality of intraluminal filter elements in a filter configuration at a location between the superior and inferior ends of the elements.
Figure 8:
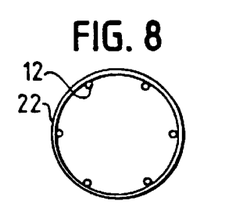
FIG. 8 is an bottom view of the filter shown in FIG. 6.

FIG. 5 shows a plurality of filter legs 12 joined by horizontal connecting members 36 such as by laser welding. Alternatively, a mesh of wires 38 may be formed by the cutting application of a laser micro machining tool. In FIG. 6, the mesh of wires 38 is formed into a stent-like, cylindrical configuration when the ends of the mesh of wires 38 are permanently laser welded together. In a preferred embodiment, the filtration device 10 must be openable to a diameter of not less than "d", preferably about 3.0 cm, yet collapsible to a diameter of less than 12 F (4.0 mm) for per cutaneous delivery via a catheter introducer system. In a preferred embodiment, the filtration device will be of length "l", preferably about 6–7 cm. As mentioned, the dual cone filter device 10 is self-anchoring on the interior of the vessel wall 28 because of the small hook or barb 32 located on the superior ends 16 and inferior ends 18, yet the blood filter device 10 will have sufficient longitudinal flexibility to pass through fifty-five (55) degrees of angulation and will not substantially distort the vessel after deployment.

Figure 9:
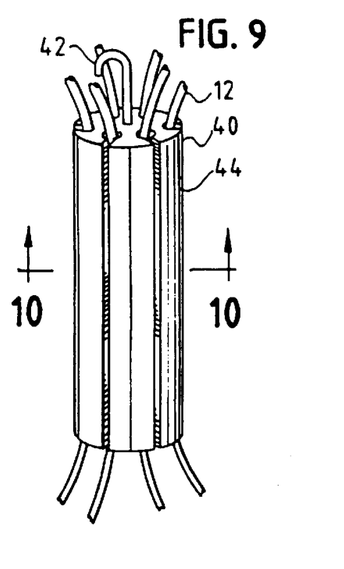
FIG. 9 is an enlarged side view of a actively releasable retainer that may be used with the filter illustrated in FIG. 1.
Figure 10:
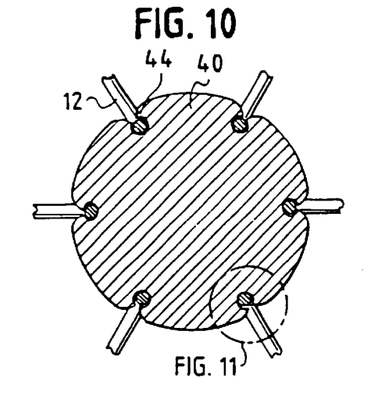
FIG. 10 is a cross-section view taken along line 10—10 of FIG. 9.
Figure 11:
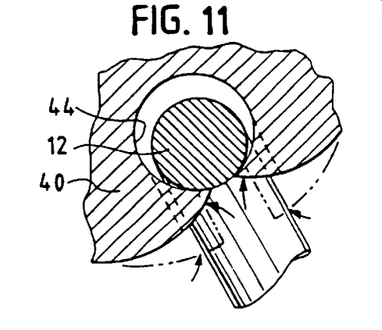
FIG. 11 is an enlarged view of the portion of the filter illustrated in the circle labeled FIG. 11 of FIG. 10.

In a preferred embodiment of the filter device 10, the dual cone filter configuration converts into an open or stent-like configuration by actively removing the releasable retainer 22. As depicted in FIG. 9, the releasable retainer 40 has a hook 42 with which it can be captured by a snare or other capturing device and pulled through a catheter for removal from the body. In this embodiment, the releasable retainer 40 is cylindrical having axially extending tubular apertures 44 extending its length into which the filter legs 12 are slidably secured until removal of the retainer 40. The releasable retainer 40 joins the filter legs 12 to form the conical filter configuration. FIG. 10 shows a cross-section of the releasable retainer 40 with the filter legs 12 secured within the apertures 44. FIG. 11 is an enlargement of the cross-sectional view of the filter leg 12 within the tubular aperture 44 of the releasable retainer 40. The diameter of the filter leg 12 is less than the diameter of the tubular aperture 44 which enables the filter leg to be slidably released from the releasable retainer 40 when the retainer 40 is snared. It will be appreciated that this construction of the filter 10 offers the possibility of providing a permanent filter, i.e., by leaving the releasable retainer 40 in place, or converting the filter 10 to the open configuration, and hence, substantially completely reopening the lumen by removing the releasable retainer 40.

Referring again to FIG. 1, the releasable retainer 22 may comprise a band of biodegradable material. Examples of such materials are polylactic acid material or polyglycolic acid suture material commonly used. The advantage of making the releasable retainer 22 from a biodegradable material is that over time the releasable retainer 22 will sufficiently degrade so as to permit the filter legs 12 to move to the open configuration. Thus, the filter device 10 passively converts from a filter configuration to a stent-like configuration. Advantageously, this conversion occurs without a subsequent invasive surgical procedure.

Figure 12:
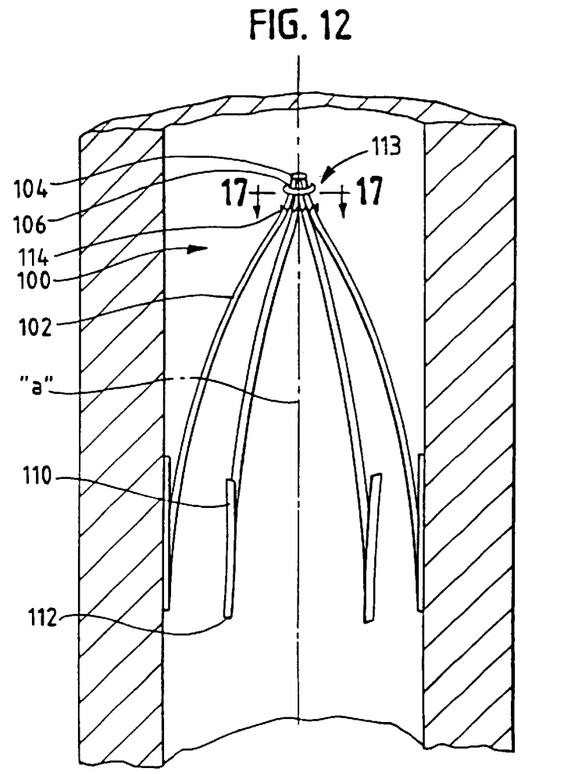
FIG. 12 is a side view of a single cone filter in a filter configuration, the filter including axially extending orientation members.

With reference now to FIG. 12, an alternate embodiment of the invention is shown in a single cone filtration device (filter) 100. The filtration device 100 may again be inserted per cutaneously into the body using the aforementioned Seldinger technique or any other commonly practiced and federally approved method of insertion.

Figure 3:
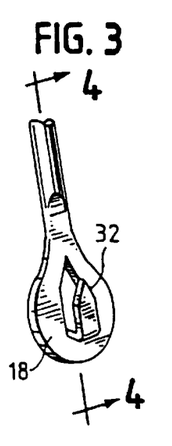
FIG. 3 is an enlarged view within the circle labeled FIG. 3 of FIG. 1 and further illustrating a small barb or hook on the end of the intraluminal filter element.
Figure 4:
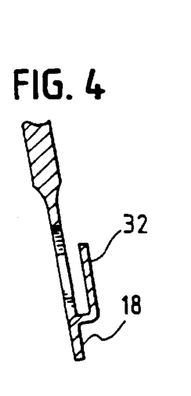
FIG. 4 is a cross-section view taken along line 4—4 of FIG. 3.

FIG. 12 shows the single cone filtration device 100 in its expanded position and having a plurality of intraluminal filter elements (filter legs) 102. The filter legs 102 are a flexible wire and, in one preferred embodiment, the wires are metallic and may be round or flattened wire. The wires may be made from a radiopaque, non-thrombogenic, and non-ferromagnetic metal meeting the certifications for permanently implanted medical devices according to the ISO and will preferably be able to withstand twelve million respiratory cycles. The wires may, in particular, consist essentially of any of the aforementioned metals described with respect to filter 10. In the filter 100 shown in FIG. 12, the filter legs 102 are made of a flattened wire. Each leg 102 has a blunted superior end 104, as discussed in the aforementioned paragraphs describing the superior and inferior positioning within the body, and has a small hook or barb 32 as seen in FIG. 3 and FIG. 4.

Figure 13:
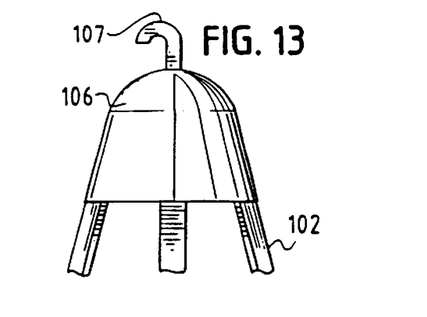
FIG. 13 is a side view of an actively releasable retainer with a hook that may be used with the filter shown in FIG. 12.
Figure 14:
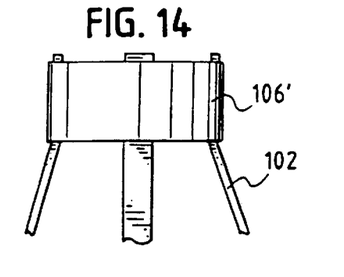
FIG. 14 is a side view of a passively releasable retainer that may be used with the filter shown in FIG. 12.

The filter 100 has a releasable retainer 106 that joins the superior ends 104 of the filter legs 102 forming a single, conical filter configuration as shown in FIG. 12. In one preferred embodiment, the retainer 106 is rounded or cap-shaped, however alternative retainer configurations could be used. Two preferred releasable filter embodiments are shown in FIG. 13 and FIG. 14. In the embodiment depicted in FIG. 13, the cap-shaped releasable retainer 106 includes a hook 107 which allows the retainer 107 to be actively removed at any time. The hook 106 may be grasped by a snare or other capturing device and the releasable retainer 106 removed from the body, thereby converting the single cone filter 100 to an open, tubular stent-like configuration. The embodiment shown in FIG. 14 has a annular ring-shaped, releasable retainer 106' which may also be removed using a snare device.

Figure 15:
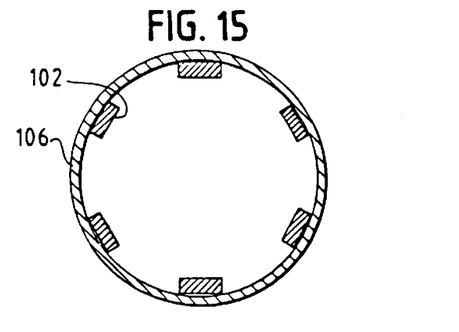
FIG. 15 is a top cross-sectional view of the restrained intraluminal filter elements contained within the releasable retainer shown in FIG. 13.
Figure 16:
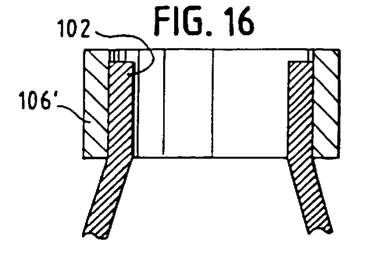
FIG. 16 is a top cross-sectional view of the restrained intraluminal filter elements contained within the releasable retainer shown in FIG. 14.
Figure 17:
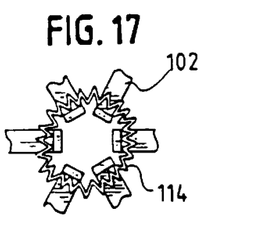
FIG. 17 is a top view of the superior end of the flat wire intraluminal filter elements joined by a spring in a restrained position.
Figure 18:
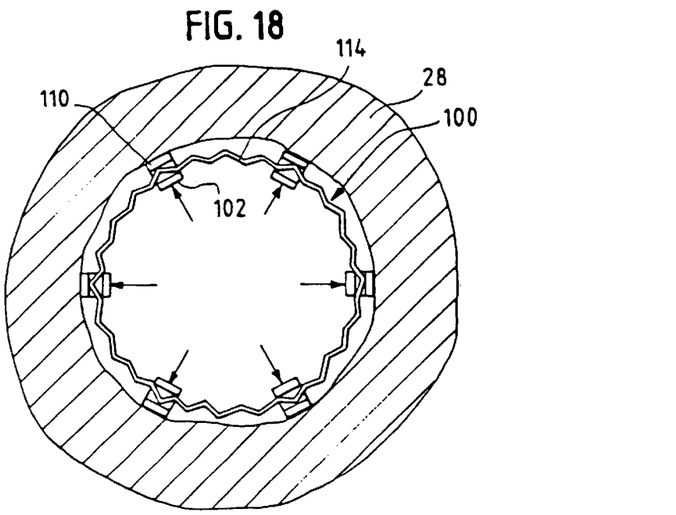
FIG. 18 is a top view of the filter shown in FIG. 12 in an open, stent-like configuration.

As is seen in FIGS. 15 and 16, the releasable retainer 106 has a hollow interior for receiving and retaining the blunted superior ends 104 of the filter legs 102. Upon release of the retainer 106, the filter legs 102 are released converting the filter 100 into an open or stent-like configuration. As seen in FIG. 15 and FIG. 16, the interior of the cap-shaped, releasable retainer 106 is hollow and holds the blunted superior ends 104 of the filter legs 102 by frictional engagement.

Referring again to FIG. 12, the releasable retainer 106 may be a band of biodegradable material such as polylactic acid material or polyglycolic acid suture material. Similar advantages as with filter device 10 are gained by making the releasable retainer 22 from a biodegradable material. Namely, the filter device 100 can be made to passively convert from a filter configuration to a stent-like configuration. Advantageously, this conversion occurs without a subsequent invasive surgical procedure.

In FIG. 12, the single cone filter 100 includes axially extending orientation members 110 to ensure centering of the filter in the vessel and to securely engage the filter with the interior wall of the blood vessel 28. Each orientation member 110 appears to be an appendix on the each inferior end 112 of each filter leg 102 which folds substantially toward the closed end of the cone 113 and is substantially aligned with an axis "a" of the filter 100. In one embodiment, each orientation member 110 may be welded or otherwise permanently connected the blunted inferior end 112 of each filter leg 102. In another embodiment, the orientation members 110 may be formed from the same wire as the filter legs 102 by forming the wire so that an acute angle is created between the filter leg portion of the wire 102 and the orientation member portion of the wire 110. Each axially extending orientation member 110 may have one or more small hook or barbs 32 located along the length of the leg 110 for engaging the interior wall of the vessel to maintain the stability and positioning of the filter 100.

As seen in FIG. 12, the filter 100 may have a spring 114 adjacent the superior ends 104 to urge them radially outward, thereby reverting the filter 100 to its stent-like configuration. The spring force required to urge the filter legs 102 to the open configuration, however, is most preferably provided by the formation of the legs themselves in combination with the respective orientation member 110. The releasable retainer 106 resists the force exerted in the legs 102 by either the spring 114, or the energy stored in the filter leg 102 itself, to retain the filtration device 100 in the single cone filter configuration. In a configuration of filter 100 not including a spring 114, an additional member may be provided to join and retain the legs together.

Figure 19:
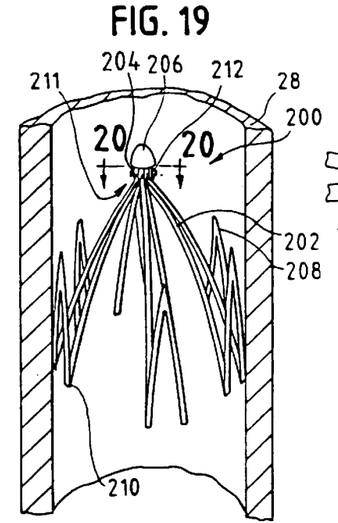
FIG. 19 is a side view of a filter in a filter configuration having axially extending orientation members.

Referring now to FIG. 19, another embodiment of the invention is shown in a single cone filtration device (filter) 200. The filter 200 may be inserted percutaneously into the body using the aforementioned Seldinger technique or by any other commonly practiced and federally approved method of insertion.

FIG. 19 shows the filter 200 in its expanded position having a plurality of intraluminal elements (filter legs) 202. In this embodiment, the filter legs 202 are a flexible wire and may be metallic and round. The wires may be made from a radiopaque, non-thrombogenic, and non-ferromagnetic metal meeting the certifications for permanently implanted medical devices according to the ISO and will preferably be able to withstand twelve million respiratory cycles. The wires may, in particular, consist essentially of any of the aforementioned metals. Each filter leg 202 has a blunted superior end 204, and has a small hook or barb 32 as seen in FIG. 3 and FIG. 4.

The filter 200 includes a releasable retainer 206 that joins the superior ends 204 of the filter legs 202 forming a single, conical filter configuration as shown in FIG. 19. In one preferred embodiment, the releasable retainer 206 is rounded or cap-shaped, however alternative retainer configurations could be used. Two preferred releasable retainers are releasable retainers 106 and 106' described above in connection with FIG. 13 and FIG. 14. Equally preferred is the use of a biodegradable retainer as discussed above. Upon release of the retainer 206, either actively with a snaring or other capturing device or passively after sufficient degradation of the biodegradable material, the filter legs 202 are released converting the filter 200 into an open or stent-like configuration.

In FIG. 19, the single cone filter 200 includes axially extending orientation members 208 to ensure centering of the filter in the vessel and to securely engage the filter with the interior wall of the blood vessel 28. Each orientation member 208 appears to be an appendix on the each inferior end 210 of each filter leg 202 which folds substantially backwards toward the tip or closed end of the cone 211. In one embodiment, each orientation member 208 may be welded or otherwise permanently connected to the blunted inferior end 210 of each filter leg 202. In another embodiment, the orientation members 208 may be formed from the same wire as the filter legs 202 by forming the wire so that an acute angle is created between the filter leg portion of the wire 202 and the orientation member portion of the wire 208. Neighboring or adjacent orientation members 208 are joined creating a wishbone-like configuration. Such a configuration assists in maintaining filter stability within the lumen. Each axially extending orientation member 208 may have one or more small hook or barbs 32 located along the length of the leg 208 for engaging the interior wall of the vessel to maintain the stability and positioning of the filter 200. In FIG. 19, the single cone filtration device 200 may have a spring 212 adjacent the superior ends 204 to urge them radially outward. Alternatively, and more preferably, the configuration of the filter legs 202 themselves in conjunction with the respective orientation member 208 provides the energy to urge the filter legs 202 to the open configuration.

Figures 20, 21:
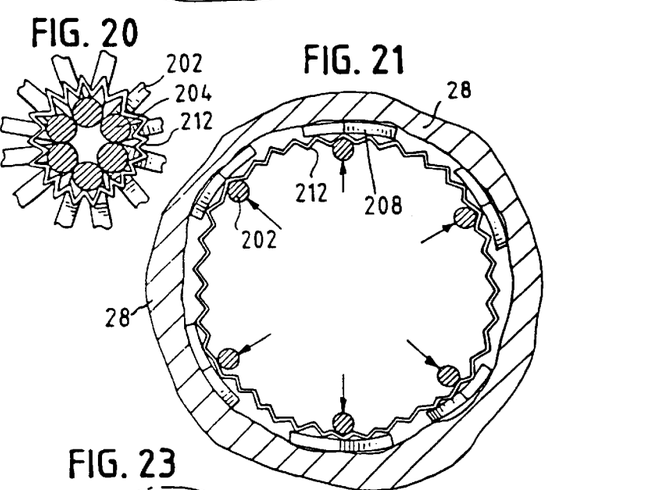
FIG. 20 is a top view of the filter shown in FIG. 19.
FIG. 21 is a top view of the filter shown in FIG. 19 in an open, stent-like configuration.

The releasable retainer 206 resists the force exerted in the legs 202 by either the spring 212 or the filter legs themselves, to retain the filtration device 200 in the single cone filter configuration. FIG. 20 shows in cross-sectional view the spring 212 attached to and joining the filter legs 202 where the releasable retainer 206 still retains the legs keeping them in a conical configuration. FIG. 21 shows a cross-sectional view of the spring 212 urging the legs radially outwardly into an open and stent-like configuration when the releasable retainer 206 is removed. The small hook 32 on each blunted superior end 204 engages the wall of the vessel for securely fixing the expanded filter within the blood vessel.

Figures 22, 23:
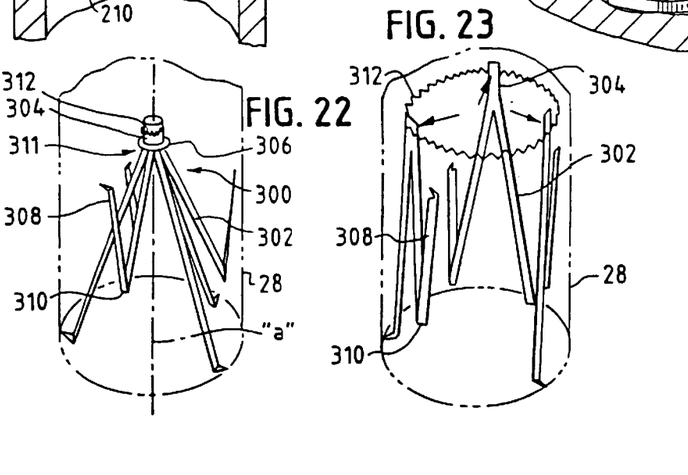
FIG. 22 is a side view of a filter in a filter configuration having axially extending orientation members.
FIG. 23 is a side view of the filter shown in FIG. 22 in an open, stent-like configuration.

Referring now to FIG. 22, in still another alternate preferred embodiment, the filtration device is a single cone filtration device 300. The filtration device 300 may be inserted percutaneously into the body using the aforementioned Seldinger technique or any other commonly practiced and federally approved method of insertion not listed herein.

FIG. 22 shows the single cone filtration device 300 in its expanded position having a plurality of filter legs 302. The legs 302 are a flexible wire and, in one preferred embodiment, the wires are metallic and round. In another embodiment, the wires may be flattened. The wires may be made from a radiopaque, non-thrombogenic, and non-ferromagnetic metal meeting the certifications for permanently implanted medical devices according to the ISO and will preferably be able to withstand twelve million respiratory cycles. The wires may, in particular, consist essentially of any of the aforementioned metals. As shown in FIG. 22, each neighboring or adjacent filter leg 302 is joined at its superior end 304. The filter 300 includes a releasable retainer 306 that joins the superior ends 304 of the filter legs 302 forming a single, conical filter configuration as shown in FIG. 22. In one preferred embodiment, the retainer 306 is rounded or cap-shaped, however alternative retainer configurations could be used as discussed above. Upon release of the retainer 306, either actively with a snaring or other capturing device or passively after sufficient degradation of the biodegradable retainer, the filter legs 302 are released converting the filter 300 into an open or stent-like configuration.

In FIG. 22, the single cone filter 300 includes axially extending orientation members 308 to ensure centering of the filter in the vessel and to securely engage the filter with the interior wall of the blood vessel 28. Each orientation member 308 appears to be an appendix on the each inferior end 310 of each filter leg 302 which folds substantially backwards toward the tip or closed end of the cone 311 and is substantially aligned with an axis "a" of the filter 300. In one embodiment, each orientation member 308 may be welded or otherwise permanently connected to the blunted inferior end 310 of each filter leg 302. In another embodiment, the orientation members 308 may be formed from the same wire as the filter legs 302 by forming the wire so that an acute angle is created between the filter leg portion of the wire 302 and the orientation member portion of the wire 308. Each axially extending orientation member 308 may have one or more small hook or barb 32 located along the length of the orientation member 308 for engaging the interior wall of the vessel to maintain the stability and positioning of the filter 300. Preferably the force necessary to move the filter legs 302 is provide by the configuration of the filter legs 302 in conjunction with the orientation members 308. However, in FIG. 22, the single cone filtration device 300 may have a spring 312 adjacent the superior ends 304 to restore the filter to its stent-like configuration by urging the filter legs 302 radially outward. The releasable retainer 306 resists the force attempting to return the filter legs 302 to the open configuration and retains the filtration device 300 in the single cone filter configuration. FIG. 23 shows the spring 312 urging the legs 302 radially outwardly into an open and stent-like configuration after the releasable retainer 306 has been removed. The small hook 32 of each blunted superior end 304 engages the interior wall of the vessel 28 to securely hold the converted filter against the wall of the vessel 28.

Figure 24:
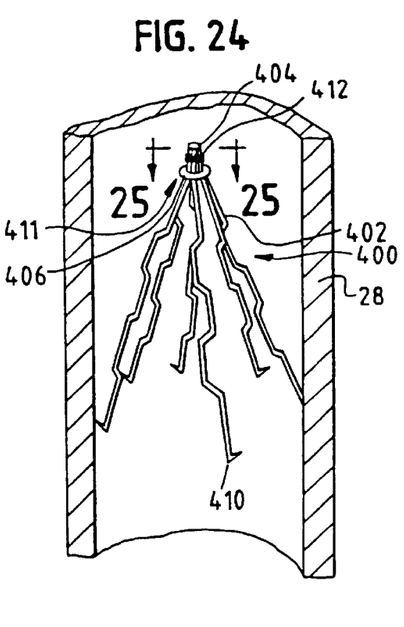
FIG. 24 is a side view of a filter in a filter configuration having a plurality of intraluminal filter elements that include a corrugated structure.

Referring to FIG. 24, in another alternate embodiment, the filtration device is a single cone filtration device 400. The filtration device 400 may be inserted percutaneously into the body using the aforementioned Seldinger technique or any other commonly practiced and federally approved method of insertion not listed herein.

FIG. 24 shows the single cone filtration device 400 in its expanded position having a plurality of filter legs 402. The legs 402 are a flexible wire and, in one preferred embodiment, the wires are metallic and round. The wires may be made from a radiopaque, non-thrombogenic, and non-ferromagnetic metal meeting the certifications for permanently implanted medical devices according to the ISO and will preferably be able to withstand twelve million respiratory cycles. The wires may, in particular, consist essentially of any of the aforementioned metals. The wire filter legs 402 are corrugated to enhance filtering of blot clots. Each leg 402 has a blunted superior end 404, as discussed in the aforementioned paragraphs describing the superior and inferior positioning within the body, and has a small hook or barb 32 as seen in FIG. 3 and FIG. 4. The filter 400 includes a releasable retainer 406 that joins the superior ends 404 of the filter legs 402 forming a single, conical filter configuration as shown in FIG. 24. In one preferred embodiment, the retainer 406 is rounded or cap-shaped, however alternative retainer configurations could be used as discussed above. Upon release of the retainer 406, either actively with a snaring or other capturing device or passively after sufficient degradation of the biodegradable retainer, the filter legs 402 are released converting the filter 400 into an open or stent-like configuration.

Figure 25:
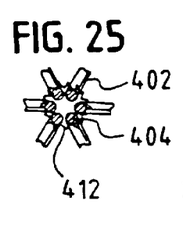
FIG. 25 is a top view of the filter shown in FIG. 24.
Figure 26:
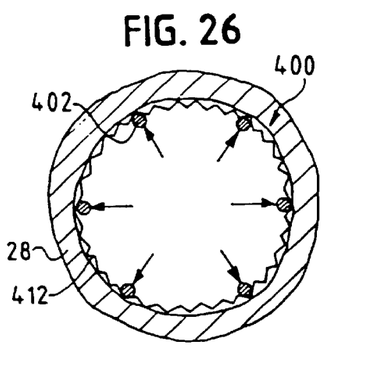
FIG. 26 is a top view of the filter shown in FIG. 24 in an open, stent-like configuration.

In FIG. 24, the single cone filter 400 may be configured to include axially extending orientation members not depicted to ensure centering of the filter in the vessel and to securely engage the filter with the interior wall of the blood vessel 28. Each orientation member appears to be an appendix on the each inferior end 410 of each filter leg 402 which folds substantially toward the closed end of the cone 411. In one embodiment, each orientation member may be welded or otherwise permanently connected to the blunted inferior end 410 of each filter leg 402. In another embodiment, the orientation members may be formed from the same wire as the filter legs 402 by forming the wire so that an acute angle is created between the filter leg portion of the wire 402 and the orientation member portion of the wire. Each axially extending orientation member may have one or more small hook or barbs 32 located along the length of the leg for engaging the interior wall of the vessel to maintain the stability and positioning of the filter 400. The configuration of the legs 402 and orientation members may provide the force necessary to revert the filter legs 402 to the open configuration. In FIG. 24, the single cone filtration device 400 may have a spring 412 adjacent the superior ends 404 to revert the filter legs 402 to the open configuration. The releasable retainer 406 resists the force exerted in the legs 402 to retain the filtration device 400 in the single cone filter configuration. FIG. 25 shows a cross-sectional view of the spring 412 attached to and joining the filter legs 402 where the releasable retainer 406 still retains the legs keeping them in a conical configuration. FIG. 26 shows a cross-sectional view of the spring 412 urging the legs radially outwardly thereby reverting them into an open and stent-like configuration when the releasable retainer 406 is removed. The small hook 32 on each blunted superior end 404 engages the wall of the vessel for securely fixing the expanded filter within the blood vessel.

Figure 27:
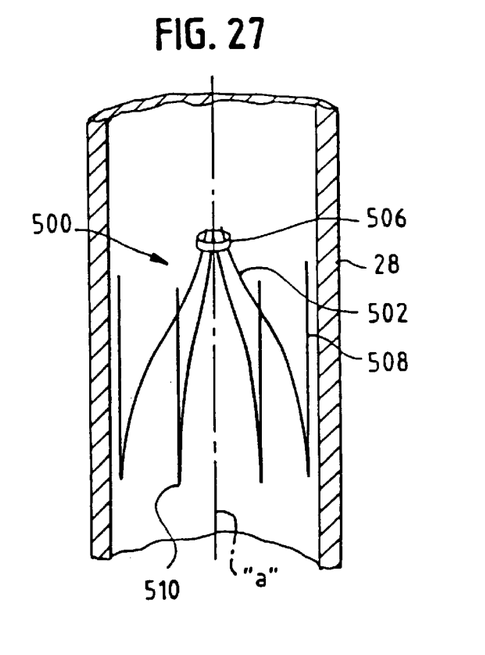
FIG. 27 is a side view of a filter in a filter configuration with a plurality of intraluminal filter elements having axially extending orientation members.
Figure 28:
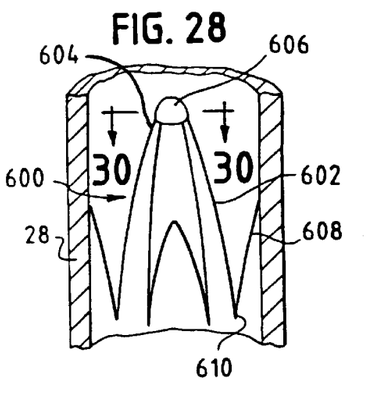
FIG. 28 is a side view of a filter in a filter configuration with adjacent intraluminal filter elements joined by axially extending orientation members.

In certain preferred embodiments of a filter device described above a spring in not needed to urge the filter legs radially outwardly to restore the filter its open configuration. In FIG. 27, the single cone filter 500 is formed substantially the same way as the single cone filter 100 shown in FIG. 12. The filter legs, releasable retainer, and orientation members are in accordance with the foregoing discussion associated with single cone filter 100. In FIG. 28, the single cone filter 600 is formed substantially the same way as single cone filter 200 shown in FIG. 19. The filter legs, releasable retainer, and orientation members are in accordance with the discussion associated with single cone filter 200. When the releasable retainer is removed from the single cone filter 500 and single cone filter 600, the filters are self-opening. Each filter leg and orientation member of filter 500 and filter 600 is formed from a single wire. The wire is bent forming a hair-pin configuration. The energy stored in wires causes the filter legs to self-open upon release of the retainer and thereby create an open or stent-like configuration.

Figure 29:
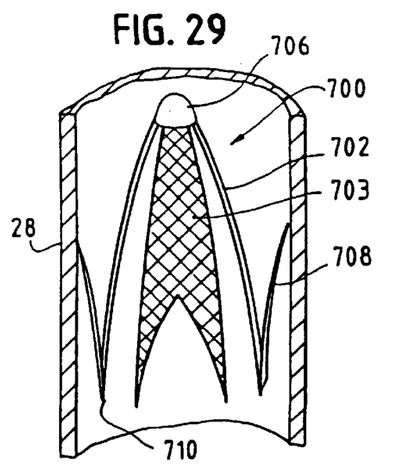
FIG. 29 is a side view of a filter in a filter configuration having adjacent intraluminal filter elements joined by a wire mesh and having axially extending orientation members.

In FIG. 29, the single cone filter 700 is constructed similarly to the aforementioned blood filters. In filter 700, each neighboring or adjacent filter legs is connected at is superior end and each neighboring or adjacent orientation member is connected. Thus, filter 700 is formed from one continuous piece of wire that has been formed into a stent-like configuration and then retained by a releasable retainer in a filter configuration. If the wire of filter 700 were broken at one point and the wire laid flat, the shape of the wire may appear similar to a sinusoidal wave. In filter 700, between each adjacent and connected filter leg, the filter legs may have a mesh of wires to enhance filtering during embolization. The meshed wires 703 are seen in FIG. 29.

Figure 30:
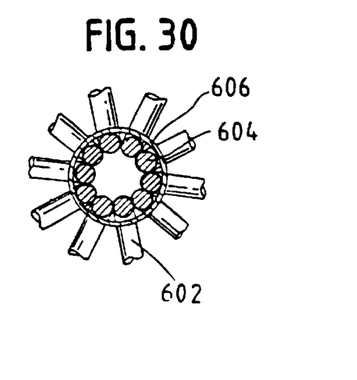
FIG. 30 is a top view of the filter shown in FIG. 29.
Figure 31:
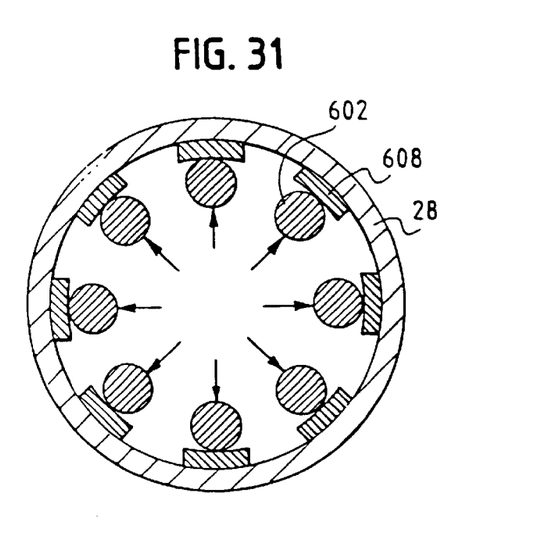
FIG. 31 is a top view of the filter shown in FIG. 29 in an open, stent-like configuration.

In accordance with the preferred embodiments, the filter legs of filters 500, 600 and 700 are retained in a releasable retainer while in the single cone configuration. The releasable retainer resists the force restoring the filter legs to the open configuration and thus retains the filter legs in the single cone filter configuration. FIG. 30 shows a cross-sectional view of the filter legs of filters 500, 600 and 700 joined or retained by a releasable retainer. FIG. 31 shows a cross-sectional view of the filter legs of filters 500, 600 and 700 expanding radially outwardly into an open and stent-like configuration when the releasable retainer is removed. A small hook 32 on each blunted superior end of each filter leg engages the wall of the vessel to securely fix the expanded filter within the blood vessel. In this expanded position, the interior of the blood vessel lumen is open for the free-flow of blood.

Figure 32:
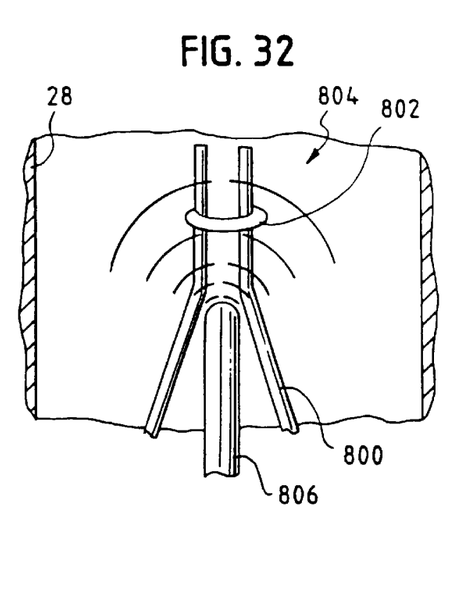
FIG. 32 is a side view of a device inserted into the lumen near a filter in a filter configuration in accordance with the invention for releasing the retainer.
Figure 33:
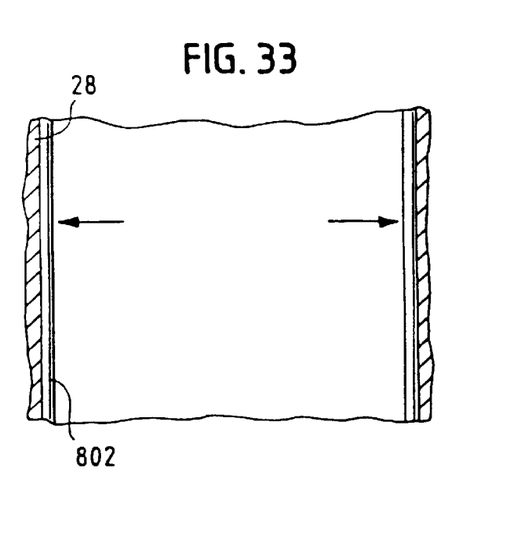
FIG. 33 is a side view of the filter shown in FIG. 32 in an open, stent-like configuration.

As mentioned previously, the releasable retainer in each of the aforementioned embodiments can be actively or passively removed. FIG. 32 shows filter legs 800 that are restrained by a releasable retainer 802 in the form of a band. The filter legs 800 form a conical filter configuration. In FIG. 32, the releasable retainer 802 is a band the engages each of the filter legs. This retainer 802 is generally biologically stabile, i.e., does not degrade within the body, until being exposed to an energy stimulus or a chemical stimulus. The waves 804 shown in FIG. 32 represent an energy stimulus. An emitter 806 is depicted by the rod-like structure in FIG. 32, but is not limited to such a structure configuration. The waves 804 given off by the emitter 806 may be an ultrasonic energy or an electrical current. In another embodiment, the emitter 806 may release waves 804 of a chemical stimulus that breaks or dissolves the retaining band 800. Preferably the band remains structurally stable until it is exposed to the either the mechanical, electrical or chemical stimulus. For example, a polymer material responsive to ultrasound energy to initiate a degradation process is described in U.S. Pat. No. 4,657,543, the disclosure of which is incorporated by reference. The retainer 802 may also be a stainless steel material that may be electrolytically disintegrated as is shown in the art. After exposure to the energy stimulus, the retainer 802 begins to degrade similar to the above-described biodegradable releasable retainers or otherwise sufficiently structurally weakens so as to permit the release of the filter legs 800. Upon release, as shown in FIG. 33, the filter legs 800 expand to form the an open or stent-like configuration when the retainer 802 degrades as a result of exposure to either an energy stimulus or a chemical stimulus.

In an alternate embodiment, any of the aforementioned filters may be made both passively self-opening and entirely biodegradable based upon the materials selected to form the filter structure. The filter itself, and particularly the intraluminal elements (filter legs) and the orientation members, where necessary, may be formed of a biodegradable material which degrades within the body after a specified period of time. Such materials are biocompatible with the body which means that they are physiologically tolerable. Preferably, such biocompatible materials do not cause undesirable physiological conditions that may result in changes in the structure and function of living tissues in the body. In one preferred embodiment, the filter may be composed essentially of the biodegradable and biocompatible material polylactic acid (pla). An alternate preferred material is the copolymer of L-lactide and .ε.-caprolactone as described in U.S. Pat. No. 5,670,161, the disclosure of which is hereby incorporated by reference. The releasable retainer used in conjunction with the filters composed substantially of biodegradable materials is made of a second biodegradable and biocompatible material. In one preferred embodiment, the releasable retainer is made of the biodegradable material polyglycolic acid (pga). The biodegradable material selected for the filter structure has a degradation rate (d1) preferably slower than a degradation rate (d2) of the biodegradable material selected for the releasable retainer. Thus, the releasable retainer will degrade or dissolve first thereby releasing the filter legs and converting the filter into a stent-like configuration. The filter legs then move into contact with the lumen walls and in relatively short period of time are incorporated by endothelial tissue. After a further period of time, i.e., the difference between the filter degradation rate (d1) and the retainer degradation rate (d2), the filter will begin to degrade within the body. A preferred first degradation rate (d1) may be up to one year while a preferred second degradation rate (d2) may be approximately 21 weeks. Advantageously, because of the biodegradable composition of the filter and the retainer, none of the filter materials will remain in the body. Thus, a filter constructed in accordance with this embodiment of the invention may be particularly preferred by surgeon wherein the risk of embolism is transient.

The invention has been described in terms of several preferred embodiments. The description of these embodiments should in no way be considered limiting of the broad scope of the invention set forth in the following claims.

I claim:

1. A filter adapted for use in treating embolism, the filter comprising:
   a plurality of intraluminal filter elements, the intraluminal filter elements arranged to be disposed in a filter configuration within the lumen of a blood vessel,
   a releasable retainer for joining the intraluminal filter elements in the filter configuration, and
   a member joined to the plurality of intraluminal filter elements which upon release of the releasable retainer joins the intraluminal filter elements in an open configuration.

2. The filter of claim 1, wherein the member comprises a spring formed integrally with the plurality of intraluminal filter elements.

3. The filter of claim 1, further comprising means for passively releasing the releasable retainer after a predetermined time period.

4. The filter of claim 1, wherein the releasable retainer comprises a biodegradable material.

5. The filter of claim 1, means for actively releasing the releasable retainer.

6. The filter of claim 1, wherein the releasable retainer comprises a coupling formed with a plurality of catches, each of the catches respectively engaged with one of the plurality of intraluminal filter elements.

7. The filter of claim 1 wherein the releasable retainer comprises a breakable band engaging each of the plurality of intraluminal filter elements.

8. The filter of claim 1, further comprising means for releasing the releasable retainer responsive to an energy stimulus.

9. The filter of claim 8, wherein the energy stimulus comprises ultrasonic energy.

10. The filter of claim 8, wherein the energy stimulus comprises an electrical current.

11. The filter of claim 1, further comprising means for releasing the releasable retainer responsive to a chemical stimulus.

12. A vena cava filter comprising:
   a plurality of intraluminal filter elements each having a superior end and an inferior end,
   a plurality of orienting members secured to and extending from respective ones of the intraluminal filter elements,
   a releasable retainer for joining the superior ends in a filter configuration, and
   a member joined to the intraluminal filter elements to restore the superior ends to an open configuration upon release of the retainer.

13. The vena cava filter of claim 12, wherein each orienting member is formed integrally with a respective intraluminal filter element.

14. The vena cava filter of claim 12, wherein each orienting member is formed integrally with the inferior end of its respective intraluminal filter element.

15. The vena cava filter of claim 12, wherein each orienting member comprises a portion of the respective intraluminal filter element extending substantially parallel to an axis of filtration.

16. The vena cava filter of claim 12, wherein each orienting member comprises an elongate portion of the respective intraluminal filter element extending from the respective superior end and radially outwardly from the retainer.

17. The vena cava filter of claim 12, wherein each orienting member comprises a loop extending between the inferior ends of adjacent intraluminal filter elements.

18. The vena cava filter of claim 12, wherein the member comprises a spring formed integrally with the intraluminal filter elements.

19. A vena cava filter comprising:
   a plurality of intraluminal filter elements each having a superior end and an inferior end,
   a first spring member secured to the intraluminal filter elements adjacent the superior ends for urging the superior ends radially outward,
   a second spring member secured to the intraluminal filter elements adjacent the inferior ends for urging the inferior ends radially outward,
   a releasable retainer for securing the intraluminal filter elements in a filter configuration, the releasable retainer being disposed at a location along the intraluminal filter elements between the superior and inferior ends.

20. The vena cava filter of claim 19, further comprising means for passively releasing the releasable retainer after a predetermined time period.

21. The vena cava filter of claim 19, wherein the releasable retainer comprises a biodegradable material.

22. The vena cava filter of claim 19, means for actively releasing the releasable retainer.

23. The vena cava filter of claim 19, wherein the releasable retainer comprises a coupling formed with a plurality of catches that respectively engage one of the plurality of intraluminal filter elements.

24. The vena cava filter of claim 19, wherein the releasable retainer comprises a breakable band engaging each of the plurality of intraluminal filter elements.

25. The vena cava filter of claim 24, further comprising means for releasing the releasable retainer responsive to an energy stimulus.

26. The vena cava filter of claim 25, wherein the energy stimulus comprises ultrasonic energy.

27. The vena cava filter of claim 25, wherein the energy stimulus comprises an electrical current.

28. The vena cava filter of claim 19, further comprising means for releasing the releasable retainer responsive to a chemical stimulus.

29. The vena cava filter of claim 19, wherein each superior end and each inferior end comprises a barb for engaging an interior vessel wall.

30. The vena cava filter of claim 19, wherein the first and second springs are formed at least in part with the plurality of intraluminal filter elements.

31. The vena cava filter of claim 29, wherein each intraluminal filter element is compressible upon release of the releasable retainer, whereby linear displacement of the superior and inferior ends is avoided.

32. A method for treating pulmonary embolism comprising the steps of:
   operatively disposing a filter in accordance with claim 1 within the inferior vena cava of a patient in the filter configuration,
   determining a passage of a risk of pulmonary embolism, and
   converting the filter, in situ, from the filter configuration to an open configuration.

33. The method of claim 32, wherein the step of converting comprises, actively releasing a retainer member securing the filter in the filter configuration.

34. The method of claim 32, wherein the step of converting comprises, providing a passively releasable retainer securing the filter in the filter configuration.

35. A filter having a filter configuration and an open configuration, the filter comprising:
   a plurality of intraluminal filter elements each having a superior end and an inferior end, the plurality of intraluminal filter elements being secured together by a member in the open configuration,
   a plurality of orienting members extending from and secured to respective ones of the intraluminal filter elements, and
   a releasable retainer for joining the superior ends whereby the intraluminal filter elements are restrained in a filter configuration.

36. The filter of claim 35, further comprising means for passively releasing the releasable retainer after a predetermined time period.

37. The filter of claim 35, wherein the releasable retainer comprises a biodegradable material.

38. The filter of claim 35, wherein the releasable retainer releases upon active intervention.

39. The filter of claim 35, wherein the releasable retainer comprises a coupling formed with a plurality of catches each of which respectively engage one of the plurality of intraluminal filter elements.

40. The filter of claim 35, wherein the releasable retainer comprises a breakable band engaging each of the plurality of intraluminal filter elements.

41. The filter of claim 35, further comprising means for releasing the releasable retainer responsive to an energy stimulus.

42. The filter of claim 41, wherein the energy stimulus comprises ultrasonic energy.

43. The filter of claim 41, wherein the energy stimulus comprises an electrical current.

44. The filter of claim 35, further comprising means for releasing the releasable retainer responsive to a chemical stimulus.

45. The filter of claim 35, wherein each orienting member is formed integrally with a respective intraluminal filter element.

46. The filter of claim 35, wherein each orienting member is formed integrally the inferior end of its respective intraluminal filter element.

47. The filter of claim 35, wherein each orienting member comprises a portion of the respective intraluminal filter element extending substantially parallel to an axis of filtration.

48. The filter of claim 35, wherein each orienting member comprises an elongate portion of the respective intraluminal filter element extending from the respective superior end and radially outwardly from the retainer.

49. The filter of claim 35, wherein each orienting member comprises a loop extending between the inferior ends of adjacent intraluminal filter elements.

50. A filter comprising:
    a plurality of intraluminal filter elements adapted to be disposed within the lumen of a blood vessel, the plurality of intraluminal filter elements comprising a first biodegradable material; and
    a releasable retainer that retains the plurality of intraluminal filter elements in a filter configuration within the lumen, the releasable retainer comprising a second biodegradable material;
    wherein upon release of the releasable retainer the plurality of intraluminal filter elements are configured to revert to an open configuration.

51. The filter of claim 50, further comprising a plurality of orienting members extending from and secured to respective ones of the intraluminal filter elements, the orienting members comprising the first biodegradable material.

52. The filter of claim 51, wherein the plurality of intraluminal filter elements and the plurality of orienting members have a predetermined degradation period.

53. The filter of claim 50, wherein the first biodegradable material comprises a material selected from the group of materials comprising polylactic acid and a copolymer of L-lactide and .ϵ.-caprolactone.

54. The filter of claim 50, further comprising means for passively releasing the releasable retainer after a predetermined time period.

55. The filter of claim 50, wherein the second biodegradable material comprises polyglycolic acid.

56. The filter of claim 50, further comprising means for releasing the releasable retainer responsive to an energy stimulus.

57. The filter of claim 50, further comprising means for releasing the releasable retainer responsive to a chemical stimulus.

58. The filter of claim 51, wherein each orienting member is formed integrally with a respective intraluminal filter element.

59. The filter of claim 51, wherein each orienting member is formed integrally with the inferior end of its respective intraluminal filter element.

60. The filter of claim 51, wherein each orienting member comprises a portion of the respective intraluminal filter element extending substantially parallel to an axis of filtration.

61. The filter of claim 51, wherein each orienting member comprises an elongate portion of the respective intraluminal filter element extending from the respective superior end and radially outwardly from the retainer.

62. The filter of claim 51, wherein each orienting member comprises a loop extending between the inferior ends of adjacent intraluminal filter elements.

* * * * *